(12) United States Patent
Geebelen

(10) Patent No.: US 9,198,760 B2
(45) Date of Patent: Dec. 1, 2015

(54) GUIDING INSTRUMENTS AND IMPACTORS FOR AN ACETABULAR CUP IMPLANT, COMBINATIONS THEREOF, METHODS FOR MANUFACTURING AND USES THEREOF

(75) Inventor: Benjamin Geebelen, Haasrode (BE)

(73) Assignee: Materialise N.V., Leuven (BE)

( * ) Notice: Subject to any disclaimer, the term of this patent is extended or adjusted under 35 U.S.C. 154(b) by 473 days.

(21) Appl. No.: 13/575,088

(22) PCT Filed: Feb. 4, 2011

(86) PCT No.: PCT/EP2011/051625
§ 371 (c)(1),
(2), (4) Date: Jul. 25, 2012

(87) PCT Pub. No.: WO2011/095575
PCT Pub. Date: Aug. 11, 2011

(65) Prior Publication Data
US 2012/0303035 A1    Nov. 29, 2012

Related U.S. Application Data

(60) Provisional application No. 61/337,550, filed on Feb. 5, 2010.

(30) Foreign Application Priority Data

Feb. 5, 2010    (GB) ................................ 1001985.9

(51) Int. Cl.
| A61B 17/58 | (2006.01) |
| A61F 2/34 | (2006.01) |
| A61F 2/46 | (2006.01) |
| A61F 2/30 | (2006.01) |

(52) U.S. Cl.
CPC .............. *A61F 2/34* (2013.01); *A61F 2/4609* (2013.01); *A61F 2002/30367* (2013.01); *A61F 2002/30378* (2013.01); *A61F 2002/30537* (2013.01); *A61F 2002/30948* (2013.01); *A61F 2002/30952* (2013.01); *A61F 2002/30962* (2013.01); *A61F 2002/30985* (2013.01); *A61F 2002/4681* (2013.01); *A61F 2002/4687* (2013.01); *A61F 2220/0033* (2013.01); *A61F 2250/0004* (2013.01)

(58) Field of Classification Search
CPC .................................................... A61F 2/4609
USPC ........................................................ 606/91
See application file for complete search history.

(56) References Cited

U.S. PATENT DOCUMENTS

| 4,135,517 A * | 1/1979 | Reale ........................ 606/86 R |
| 5,141,680 A | 8/1992 | Almquist et al. |

(Continued)

FOREIGN PATENT DOCUMENTS

| DE | 10148022 A1 | 5/2003 |
| EP | 1442729 A1 | 8/2004 |
| JP | 2007056337 A | 2/2007 |

OTHER PUBLICATIONS

The International Search Report dated Jul. 26, 2011 for PCT Application No. PCT/EP2011/051625.

(Continued)

*Primary Examiner* — Nicholas Woodall

(57) ABSTRACT

The invention relates to guiding instruments (1) for guiding an acetabular cup implant as well as to impactors (13) for press-fitting an acetabular cup implant, both of which are of use during reconstructive joint surgery, more specifically during reconstructive hip joint surgery. The guiding instruments are characterized in that they fit onto an acetabular cup implant (8) and are designed to fit onto specific areas of the pelvic bone ensuring a unique fit on the bone. The impactors are characterized in that a fixation element (15) is connected to the stem (14) of the impactor by a ball joint. The invention also relates to combined guiding and fitting elements for an acetabular cup implant, comprising a guiding instrument and an impactor.

15 Claims, 10 Drawing Sheets

(56) References Cited

U.S. PATENT DOCUMENTS

| | | | |
|---|---|---|---|
| 5,192,539 A | 3/1993 | Van Der Marel et al. | |
| 5,989,293 A * | 11/1999 | Cook et al. | 623/22.29 |
| 6,682,567 B1 | 1/2004 | Schroeder | |
| 7,727,282 B2 * | 6/2010 | Slone et al. | 623/22.12 |
| 8,172,851 B2 * | 5/2012 | Ward et al. | 606/92 |
| 2004/0153063 A1 | 8/2004 | Harris, Jr. | |
| 2005/0021148 A1 * | 1/2005 | Gibbs | 623/22.12 |
| 2005/0148843 A1 * | 7/2005 | Roose | 600/407 |
| 2007/0173856 A1 | 7/2007 | Parker | |
| 2008/0255568 A1 * | 10/2008 | Tornier et al. | 606/91 |
| 2009/0163922 A1 | 6/2009 | Meridew et al. | |
| 2009/0265009 A1 * | 10/2009 | Ward et al. | 623/18.11 |
| 2010/0016984 A1 | 1/2010 | Trabish | |
| 2011/0208202 A1 * | 8/2011 | Zumsteg et al. | 606/91 |

OTHER PUBLICATIONS

The International Preliminary Report on Patentability dated Mar. 27, 2012 for PCT Application No. PCT/EP2011/051625.

* cited by examiner

GUIDING INSTRUMENTS AND IMPACTORS FOR AN ACETABULAR CUP IMPLANT, COMBINATIONS THEREOF, METHODS FOR MANUFACTURING AND USES THEREOF

CROSS-REFERENCE TO RELATED APPLICATIONS

This application is a U.S. national phase of PCT Application No. PCT/EP2011/051625, filed Feb. 4, 2011, which claims priority to U.S. Application No. 61/337,550, filed Feb. 2, 2010 and GB Application No. 1001985.9, filed Feb. 5, 2010.

FIELD OF THE INVENTION

The present invention relates to guiding instruments for guiding an acetabular cup implant as well as to impactors for press-fitting an acetabular cup implant, both of which are of use during reconstructive joint surgery, more specifically during reconstructive hip joint surgery. The present invention also relates to combined guiding and fitting elements for an acetabular cup implant, comprising a guiding instrument and an impactor.

BACKGROUND

In most joint arthroplasty, replacement and/or reconstruction surgery procedures, and in particular in hip joint surgery, the joint is replaced by a prosthetic implant. The main goal of such interventions is to relieve (arthritic) pain and/or to restore severe physical joint damage. When a prosthesis fails, a revision surgery is carried out. However, this procedure is technically more difficult and time-consuming than the primary intervention and the outcome is often less satisfactory, both because there is less bone stock to work with and because the removal of adherent cement or prosthetic components may result in fracture or perforation of the bone. Furthermore, with each successive joint revision, the risk of infection and symptomatic loosening of the prosthesis may increase substantially. Accordingly, one of the most important aspects of joint surgery procedures is the correct, accurate and stable placement of the primary implant.

The majority of acetabular implants used in hip surgery are currently placed using the press-fit technique. In this technique, the patient's acetabulum is first reamed with a sequence of hemispherical reamers with increasing diameters, such that a hemispherical cavity is created at the location where the implant should be placed. However, the final largest reamer typically still has a diameter smaller than that of the implant. In a further step, the implant is attached to an impactor and placed upon the pelvis of the patient, such that the implant supports on the rim of the reamed cavity and the orientation of the implant is anatomically suitable. Finally, the impactor is hit with a hammer until the implant sits inside the reamed cavity. Thereafter, the implant is released from the impactor.

Although the general consensus in the field is that the correct and accurate orientation of the acetabular implant determines the success of the surgery and the lifespan of the implant (Hayakawa, Keiko, et al. Archives of orthopaedic and trauma surgery 129.9 (2009):1151-6), the above-described procedure shows several shortcomings in this regard. Indeed, the only anatomical visual reference during final placement is the orientation of the transverse ligament (Pearse, C J., et al. Hip international 18.1 (2008):7-10), to which the top plane of the implant should be oriented in parallel. Accordingly, rotation around the axis of the transverse ligament remains a variable parameter. In addition, the transverse ligament is generally obscured from the surgeon's view, further hampering the orientation process. Furthermore, the impactor and hammer are both rather bulky, making it difficult to keep the impactor in a stable orientation.

In the past, few solutions have been proposed for these problems.

US patent application 2009/0163922 A1 (Meridew, Metzger) describes a patient-specific guide to be positioned and optionally attached to the acetabular rim, designed to interface with the impactor so as to enforce the correct orientation. However, such a device does not have the rigidity and strength to be able to withstand the momentum applied to it during impaction.

Japanese patent application 2007-056337 (Hananouchi) describes a patient-specific guide for inserting a pin into the acetabular rim, which can then be used by the surgeon as a visual reference to which the impactor is kept in a parallel position. However, such a system only provides visual but no mechanical guidance.

Accordingly, there is a need for alternative and improved surgical devices, and in particular surgical guiding instruments, which provide the ability to correctly and accurately insert, place and orient an implant into a patient's joint. More specifically, there is a need for alternative and improved surgical guiding instruments to correctly and accurately place an acetabular cup implant into a patient's acetabulum during hip joint surgery.

SUMMARY OF THE INVENTION

The present invention provides surgical devices for joint implants, which ensure a correct, accurate and stable placement and orientation of an implant into the joint. More particularly, the present invention provides guiding instruments as well as impactors and combinations thereof, allowing accurate and stable insertion of an acetabular cup implant into a patient's acetabulum during hip joint surgery procedures.

In a first aspect, the present invention provides guiding instruments for an acetabular cup implant which comprise (i) a support structure which fits securely onto an acetabular cup implant and (ii) one or more contact elements which fit tightly onto the patient-specific morphology of areas of the bone surrounding the acetabular cup implant zone in at least three contact points. More particularly, the contact elements of the guiding instruments according to the present invention are designed in such a way that the angle between the plane through the central axis of the implant and one contact point and the plane through the central axis and the adjacent contact point is never greater than 180°. In addition, the contact elements of the guiding instruments according to the present invention are designed in such a way that, upon contacting the corresponding areas of the bone surrounding the acetabulum, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum The guiding instruments of the invention further comprise one or more locking features. More particularly, the locking features allow an interlock of the guiding instruments of the invention with an implant and/or with an impactor for placement of the implant.

In particular embodiments, the guiding instruments according to the invention, and more particularly the contact elements thereof, are designed such that, upon placement of the guiding instrument in the acetabular implant zone, the guiding instrument and the acetabular cup implant are either forced to or can be made to rotate around the guiding instrument's and the implant's center point until the implant has the desired orientation with respect to the pelvis.

In certain embodiments, the guiding instruments according to the invention further comprise a positioning feature, such as a hole or slot, allowing the passage of a positioning device positioned in the bone surrounding the acetabulum. In these specific embodiments, the positioning device can for example be a pin positioned in the bone surrounding the acetabulum.

In further particular embodiments of the present invention the contact elements comprised in the guiding instruments of the invention form larger contact surfaces extending over specific areas of the bone surrounding the acetabulum that comprise two or more contact points.

The guiding instruments of the present invention may be medical-image-based patient-specific guiding instruments or may be modular devices comprising elements that can be adjusted to the shape of the bone, or combinations thereof.

A further aspect of the present invention provides combinations of an acetabular cup implant and a guiding instrument according to the present invention, wherein the guiding instrument comprises (i) a support structure which fits securely onto the acetabular cup implant and (ii) one or more contact elements which fit tightly onto the patient-specific morphology of areas of the bone surrounding the acetabular cup implant zone in at least three contact points. More particularly, the contact elements of the guiding instruments according to the present invention are designed in such a way that the angle between the plane through the central axis of the implant and one contact point and the plane through the central axis and the adjacent contact point is never greater than 180°. In addition, in particular embodiments, the contact elements of the guiding instruments of the combinations according to the present invention are designed in such a way that, upon contacting the corresponding areas of the bone surrounding the acetabulum, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum. In particular embodiments, the guiding instruments of the invention comprise one ore more locking features which can ensure an interlock with the acetabular cup implant and/or an impactor.

In yet a further aspect, the present invention provides impactors for fitting an acetabular cup implant, which comprise (i) a stem comprising a drive member, a hinge element and an impact element and (ii) a fixation element which locks onto an implant and/or onto a guiding instrument for an implant by means of one or more locking features. In particular embodiments, the fixation element comprises one or more hooks which can interlock with an implant and/or a guiding instrument for an implant. In the impactors according to the present invention, the hinge element of the stem forms a ball joint with the fixation element allowing movement of the orientation of the stem relative to the fixation element. The connection of the ball joint in the fixation element forms a hinge which provides the impactor with a large rotation capacity and a high degree of angular freedom.

In certain specific embodiments, the impactors of the present invention may further comprise a locking element that can limit or fully block the movement of the stem relative to the fixation element and/or a mechanism to easily release the guiding instrument and/or implant.

The present invention further provides combinations of an acetabular cup implant and an impactor and optionally a guiding instrument, whereby the impactor comprises (i) a stem comprising a drive member, a hinge element and an impact element and (ii) a fixation element which locks onto the implant and/or onto the guiding instrument for the implant by means of one or more locking features. In particular embodiments, the impactor is characterized in that the hinge element of the stem forms a ball joint with the fixation element allowing movement of the orientation of the stem relative to the fixation element.

In yet a further aspect, the present invention provides a combined guiding and fitting element for an acetabular cup implant, which comprises a guiding instrument and an impactor according to the present invention, wherein said guiding instrument and said impactor can interlock by means of one or more locking features. Accordingly, the guiding instrument of the combined guiding and fitting element comprises (i) a support structure which fits securely onto an acetabular cup implant and (ii) one or more contact elements which fit onto the patient-specific morphology of areas of the bone surrounding the acetabular cup implant zone in at least three contact points, wherein the contact elements are designed in such a way that the angle between the plane through the central axis of the implant and one contact point and the plane through the central axis and the adjacent contact point is never greater than 180° and that, upon contacting the corresponding areas of the bone surrounding the acetabulum, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum The guiding instruments of the invention can interlock with the acetabular cup implant by means of one or more locking features. In certain embodiments, these one or more locking features form part of the guiding instrument and/or of the impactor. In addition, the impactor of the combined guiding and fitting element according to this aspect of the invention comprises (i) a stem comprising a drive member, a hinge element and an impact element and (ii) a fixation element which locks onto the implant and/or onto a guiding instrument for the implant, wherein the hinge element of the stem forms a ball joint with the fixation element allowing movement of the orientation of the stem relative to the fixation element and wherein the fixation element of the impactor interconnects with the guiding instrument.

In certain specific embodiments of the combined guiding and fitting element according to the present invention, the contact elements of the guiding instrument are designed such that, upon placement of the guiding instrument, the guiding instrument and the acetabular cup implant are forced to or can be made to rotate around the center point of the guiding and fitting element (and/or of the implant) to ensure the secure fit of the contact elements, such that the implant has the desired orientation with respect to the acetabulum of the pelvis.

In further embodiments of the combined guiding and fitting element according to the present invention, the guiding instrument may further comprise a positioning feature, such as a hole or slot, allowing the passage of a positioning device positioned in the bone surrounding the acetabulum. In these specific embodiments, the positioning device can for example be a pin positioned in the bone surrounding the acetabulum.

In further particular embodiments of the combined guiding and fitting element according to the present invention, the one or more contact elements comprised in the guiding instrument may form larger contact surfaces extending over specific areas of the bone surrounding the acetabulum and comprising two or more contact points.

The guiding instruments, comprised in the combined guiding and fitting elements according to the present invention may be medical-image-based patient-specific guiding instruments but may also be modular instruments comprising one or more standard parts that can be adjusted to the shape of the bone.

In yet a further aspect of the present invention, combinations of an acetabular cup implant and a combined guiding and fitting element for an acetabular cup implant according to the invention are provided. More particularly, in these combinations, the guiding and fitting element comprises (a) a guiding instrument for the acetabular cup implant comprising (i) a support structure which fits securely onto an acetabular cup implant and (ii) one or more contact elements which fit onto areas of the bone surrounding the acetabular cup implant zone in at least three contact points, wherein the contact elements are designed in such a way that the angle between the plane through the central axis of the implant and one contact point and the plane through the central axis and the adjacent contact point is never greater than 180° and that, upon contacting the corresponding areas of the bone surrounding the acetabulum, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum, and (b) an impactor which comprises (i) a stem comprising a drive member, a hinge element and an impact element and (ii) a fixation element which locks onto the implant and/or onto a guiding instrument for the implant, wherein the hinge element of the stem forms a ball joint with the fixation element allowing movement of the orientation of the stem relative to the fixation element and wherein the fixation element of the impactor interconnects with said guiding instrument. The combined guiding and fitting elements of the invention can interlock with the acetabular cup implant by means of one or more locking features. In specific embodiments of the invention, these one or more locking features are part of the guiding instrument and/or impactor and of the implant.

According to particular aspects of the present invention, a guiding instrument, an impactor and an implant are interconnected with each other prior to placement of the implant into the acetabular cup implant zone of the pelvic bone. The guiding instrument present on the implant upon placement thereof in the acetabulum ensures the correct positioning of the implant.

To further ensure a correct and stable orientation of the implant into the joint, the guiding instruments according to particular embodiments of the invention are designed in such a way that, upon insertion of the implant, the implant is forced to rotate around its center point into the desired and correct orientation. This is achieved in particular embodiments by fitting, engaging or coinciding at least three contact elements of the guiding instruments with at least three surfaces present on the bone of the pelvis surrounding the patient's acetabulum.

The surgical devices for placing joint implants, i.e. guiding instruments, impactors and combinations thereof, according to the present invention allow for a much more accurate and stable orientation of an acetabular cup implant into the patient's acetabulum in comparison with the known surgical tools currently used in hip joint surgery.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

Figure 1:
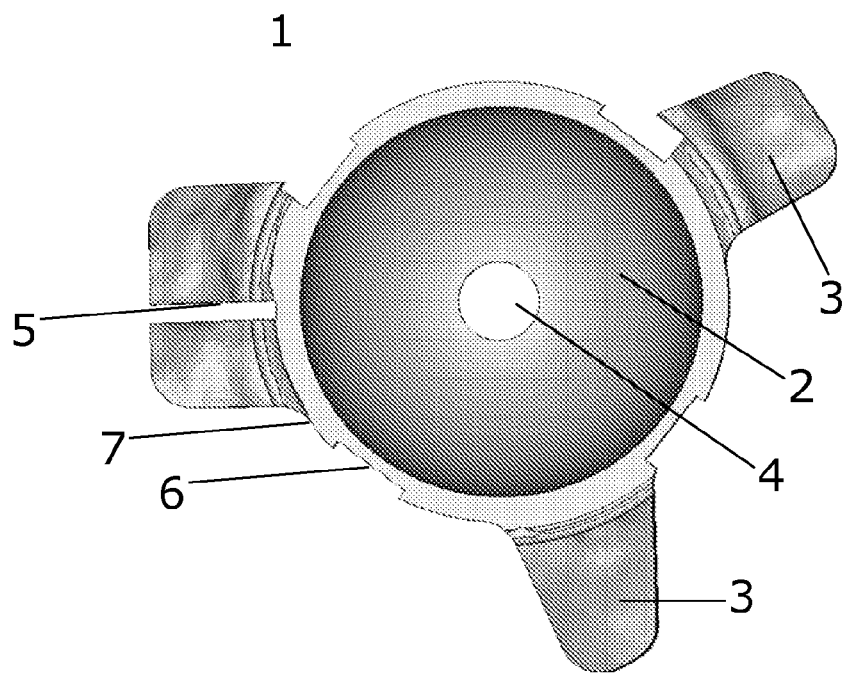
FIG. 1 Guiding instrument for an acetabular cup implant according to a particular embodiment of the invention (view from below), comprising support structure (2) comprising guide cup and ring structure (7) and further comprising contact elements (3). Support structure further comprises guide opening (4), positioning feature (5) and locking features (6).

LIST OF REFERENCE NUMERALS USED IN THE FIGURES (1) guiding instrument
(2) support structure
(3) contact element
(4) guide opening
(5) positioning feature
(6) locking feature
(7) ring structure (part of the support structure)
(8) acetabular cup implant
(9) rim of the acetabular cup implant
(10) locking feature
(11) pelvic bone
(12) outer surface of the implant
(13) impactor
(14) stem
(15) fixation element
(16) drive member
(17) impact element
(18) opening of the fixation element
(19) locking feature
(20) hinge element
(21) locking element

DETAILED DESCRIPTION

The present invention will be described with respect to particular embodiments but the invention is not limited thereto but only by the claims. Any reference signs in the claims shall not be construed as limiting the scope thereof.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

The present invention provides surgical devices for joint implants, which facilitate a correct, accurate and stable placement and orientation of an implant into the joint. More particularly, the present invention provides guiding instruments as well as impactors and combinations thereof, providing the ability to accurately and stably insert an acetabular cup implant into a patient's acetabulum during hip joint surgery procedures.

In a first aspect, the present invention provides surgical guiding instruments for guiding an acetabular cup implant, which allow both a correct and accurate orientation as well as a stable introduction of the implant into the patient's acetabulum.

More particularly, the present invention provides surgical guiding instruments that fit onto an acetabular cup implant and are secured onto the acetabular implant prior to the placement thereof into the acetabulum (more particularly the cavity provided on the location where the implant should be placed). This is ensured by a combination of a support structure and one or more contact elements which ensure a tight fit of the guiding instrument with the implant and a specific fit of the guiding instrument with the acetabulum.

The guiding instruments according to the present invention thus comprise a support structure which fits securely onto an acetabular cup implant. The support structure serves to allow a stable guidance and optimal orientation of the implant. Moreover, as the guiding elements of the present invention are in particular embodiments intended for use as an interface between the implant and an impactor, the guiding element ensures full transfer of the impact force applied by an impactor to the implant upon inserting the implant into the joint.

In particular embodiments, the outer surface (i.e. the surface facing the implant) of the support structure of the guiding elements according to the invention comprises a part which is designed to correspond as closely as possible with the hemispherical inner surface of the acetabular implant (i.e. the surface which replaces the acetabular cup of the patient, which is the surface of the implant opposite the surface contacting the acetabular bone). This part of the support structure is also referred to as the guide cup. In particular embodiments it is envisaged that the guide cup corresponds to a single hemispherical structure. However, the guide cup may also comprise a third of a surface area of a sphere, a quarter of the surface area of a sphere or any other portion of the surface of a hemisphere. Additionally or alternatively, the guide cup may comprise multiple elements which as a whole provide a rigid support for the acetabular implant cup. In further particular embodiments the outer surface of the guide cup is completely complementary to the surface of the implant cup. In more particular embodiments, this complementarity involves a clearance between the guide cup and the implant.

In specific embodiments, a full three-dimensional coverage of the contact area between the support structure of the guiding instruments of the invention and the acetabular implant ensures the stability of the guiding instruments positioned onto the implant by preventing translation and (optionally) rotation along and/or around a certain axis.

In particular embodiments, the guide cup of the support structure of the guiding instrument is a hollow structure, whereby the inner surface of the cup is designed to fit with the outer surface of (the fixation element of) an impactor. In further particular embodiments, this outer surface is a hemispherical outer surface. In further particular embodiments, the guide cup is designed to fit with an impactor according to the present invention as described herein below.

In addition to the guide cup, the support structure of the guiding instruments according to the present invention typically contains a structure which fits onto the rim of the acetabular cup implant and serves as a connecting structure, interconnecting at least three contact elements of the guiding instrument (described in detail herein below). This part of the support structure is typically circular, as an extension of the guide cup fitting onto the rim of the acetabular cup implant and is also referred to herein as the ring structure. However, the "ring structure" may also be a discontinuous structure.

The support structure of the guiding instruments according to the invention, more particularly the guide cup, may contain one or more guide holes, i.e. openings or bores. The guide hole can serve to allow a direct transfer of the impact force from the impactor to the implant. Independently thereof, one or more guide holes may also serve as a fixation element, which helps to ensure a tight interlock between the guide and an impactor and/or the implant.

Indeed, in particular embodiments, the support structure of the guiding instruments according to the invention may comprise one or more locking features, which allow or ensure an interlock with an impactor. In particular embodiments, where the impactor comprises a fixation element as described herein, the support structure of the guiding instruments comprises one or more locking features which allow an interlock with locking features of the fixation element. Such locking features present on the guiding instrument include but are not limited to grooves, slots etc, which allow interlocking e.g. with hooks or other types of extensions present on the fixation element of the impactor. In particular embodiments the guide hole of the guiding element also serves as a locking feature which interlocks with a protrusion on the fixation element of the impactor which functions as a locking feature. Other combinations of features which can function as locking features will be known to the skilled person. More particularly it can be envisaged that locking features are provided which are separate features not attached to either guiding instrument, impactor or implant but nevertheless ensure an interlock between two or more of these elements.

Thus, in particular embodiments, the combined guiding and fitting element comprises one or more locking features which allow or ensure an interlock between the guiding instrument and/or the impactor and the implant. Such locking features present on the combined guiding and fitting elements of the invention include but are not limited to hooks, pins, screws, snap-fits, clamps, clasps, jaws, pincers, plugs, cramps and cramp-irons.

In further particular embodiments the one or more locking features are designed to allow easy release of the implant from the impactor or fixation element thereof by a mechanism which is provided as part of the locking features and/or the impactor. Non-limiting embodiments of suitable systems for releasing an acetabular cup implant from an impactor are described, for example in US20040153063 and US20070173856.

In particular embodiments, the support structure of the guiding instruments according to the invention may comprise one or more locking features, which ensure an interlock with an acetabular cup implant. These may be separate from or may be associated or combined with the locking features which ensure an interlock with the impactor, described above. Such locking features can be positioned on the ring structure which extends over the rim of the acetabular cup implant, so as to ensure a specific interlock with the rim of the implant. The one or more locking features may be three-dimensional features designed specifically on the guiding instrument/implant combination, but may also be locking features which allow interlock of a patient-specific or standard guide with a patient-specific or standard implant.

The support structure of the guiding instruments of the present invention may further comprise one or more features for visual referencing to further reduce eventually remaining orientation problems. In particular embodiments these visual references are located on the ring-part of the support structure which is designed to fit on the acetabular rim of the implant.

The guiding instruments according to the present invention further comprise one or more contact elements which in at least three contact points thereon fit, engage or coincide with three or more areas of the pelvis bone surrounding the acetabular cup implant zone by means of a unique and tight fit, which is ensured by the complementarity between at least one of the one or more contact elements and the patient-specific morphology of the specific areas of the bone surrounding the acetabulum. In particular embodiments, the one or more contact elements of the guiding instruments of the invention extend over specific areas of the bone at least one, such as at least two, or three or more different directions, to further ensure the stability of the position of the guiding instruments onto the pelvis bone. Indeed, in particular embodiments the guiding instrument is designed based on information obtained from patient-specific medical images of the ischium, ilium and/or the pubis and uniquely matches with the specific bone geometry of the ischium, ilium and/or the pubis of the patient on which it is introduced resulting in the patient-specific nature of the guiding instrument.

In this way, the surgical guiding instruments according to the present invention allow for an accurate and stable orientation and fit of the acetabular cup implant into the patient's acetabulum.

In particular embodiments, the contact elements of the guiding instruments according to the invention are designed in such a way that, upon insertion of the implant, the guiding instrument forces the implant to rotate in the desired orientation into the acetabulum with respect to the pelvis bone. In particular embodiments, this is ensured by the fact that the one or more contact elements fit, engage or coincide with surfaces on the bone surrounding the acetabulum. In further specific embodiments, the three-dimensional fit between the contact elements of the guiding instruments and the specific areas of the patient's pelvis bone surrounding the acetabular cup implant zone ensures the stability of the guiding instrument by preventing both translation and rotation (either uni- or bi-directionally) along and/or around a certain axis.

In order to ensure stability of the guiding instrument, the contact points of the one or more contact elements are positioned such that the angle between the plane through the central axis of the implant and one contact point and the plane through the central axis and the adjacent contact point is less than or equal to 180°. In particular embodiments, this is ensured by the presence of at least three contact elements, whereby the angle between the plane through the central axis of the implant and one contact element and the plane through the central axis and the adjacent contact element is less than or equal to 180°. More particularly, it is envisaged that the guiding instruments comprise three contact elements which comprise contact points which are separated by an angle of about 120°. The contact elements typically span larger surfaces such that the distance between each the different contact elements is less than 120°. In particular embodiments the contact elements are provided such that one contact elements comprises a surface which spans more than one of these contact points. Accordingly, in specific embodiments, the guiding instruments of the present invention effectively comprise one or more larger contact surfaces which span a surface corresponding to more than 120° of the bone around the central axis of the implant.

In particular embodiments, the guiding instruments of the present invention are modular instruments which comprise contact elements which can be adjusted to fit securely onto the pelvis bone surrounding the acetabular cup zone. For instance, in particular embodiments, the contact elements comprise individually adjustable elements which either prior to or during fixation are fitted onto the pelvic bone to ensure a tight fit onto the acetabulum. More particularly, the contact elements are elements which are movably connected to a central support structure and can be adjusted in height and/or can rotate relative the central axis of the implant to ensure the most accurate fit with the particular parts of the pelvic bone.

In particular embodiments, one or more of the contact elements of the guiding instruments of the present invention are fixed and positioned to ensure a correct fit with a corresponding structure of the pelvic bone.

In particular embodiments, at least one of the contact elements of the guiding instruments of the present invention comprises, at the contact point, a patient-specific surface on the side facing the pelvis bone, which is exactly and fully complementary, i.e. fits specifically onto a specific anatomical area of the patient's pelvis bone surrounding the acetabular cup implant zone. This can be ensured by pre-operative planning based on images of the (reamed) acetabular cup zone. In further particular embodiments, this specific fit may involve a clearance between the surface of the contact elements and the bone, such as for example a clearance between the surface of the contact elements and the bone of between 0.1-1.0 mm. When the patient-specific surfaces of the contact elements are contacted with or positioned opposite to their corresponding complementary surfaces of the patient's pelvis bone, the surfaces fit, mate and/or engage, thereby fixing the guiding instrument, and thus also the implant connected or attached thereto, into the correct and desired position.

Typically, a patient-specific surface of a contact element is selected based on anatomical features present on the pelvis bone surrounding the implant zone. In particular embodiments a patient-specific surface is selected based on anatomical features present on one or more of the ilium part, the pubis part and the ischium part of the pelvic bone. However, it is also envisioned in particular embodiments, that features are introduced onto the patient's bone to allow the generation of patient-specific surfaces on the contact elements based thereon.

In particular embodiments as detailed above, the one or more contact elements of guiding instruments according to the invention are designed such that, upon placement of the guiding instrument, the guiding instrument and the acetabular cup implant (which are attached to each other or interconnected) can be manipulated to rotate around the implant's center point or central axis until the implant has the desired orientation with respect to the pelvis. According to these specific embodiments a rotation around the implant's center point or central axis ensures that the one or more contact elements assume their correct position, i.e. ensure a fit or interlock between the (patient-specific) areas of the one or more contact elements of the guiding instruments and the corresponding anatomical areas of the patient's pelvis bone surrounding the acetabular cup implant zone. In these embodiments, the stability of the guiding instrument is ensured by preventing both translation and rotation (either uni- or bi-directionally) along and/or around the central axis of the implant.

Apart from the requirement that they ensure a secure fit onto the pelvic bone, the size and shape of the contact elements of the guiding instruments according to the present invention are not critical to the invention. Typically the size and shape of the contact elements of the guiding instruments according to the present invention are determined by the three-dimensional surface of the pelvis bone surrounding the acetabular cup implant zone, more particularly of the pelvis bone surrounding the acetabular cup implant zone of the patient for which it is designed. In particular embodiments, the contact elements correspond to flanges, i.e. longitudinal structures which extend from the support structure of the guiding instruments of the invention in different directions and allow for a stable fitting of the guiding instruments onto the pelvis bone. In further particular embodiments the flanges extend in the direction of the ilium, ischium and the pubis, respectively. According to these embodiments, guiding instruments with at least three, more particularly guiding instruments with three flanges, are envisaged. As detailed above, the flanges are typically connected (at least) through the support structure of the guiding instruments according to the present invention.

In certain embodiments, the guiding instruments according to the invention may further comprise one or more positioning features allowing the passage of or connection to a positioning device. Typically, such a positioning device is introduced in the bone surrounding the acetabulum in a planned position prior to insertion of the implant, and insertion of or connection to the positioning device facilitates the placement of the guiding instrument. Optionally, the positioning device is inserted into the bone by positioning the guiding instrument according to the invention onto the pelvic bone prior to the placement of the implant, whereby the one or more positioning feature(s) allow positioning of the positioning device into the bone. In particular embodiments, the positioning feature is a hole, a cannula, a channel or a slot, which allows the passage of a positioning device such as a guiding pin. In particular embodiments, the feature comprises at least a cylindrical hole. Additionally or alternatively, the positioning feature comprises a clasp or other fixation element which allows connection to a positioning device, such as a guiding pin.

More particularly the nature of the one or more positioning features of the guiding instruments (i.e. actual height or distance relative to the surface of the bone) is determined to ensure an adequate guidance of the guiding instrument by the positioning device or visa versa.

As detailed above, in particular embodiments the positioning feature in the guiding instrument is also designed for use in the placement of the positioning device in the bone prior to placement of the implant into the bone. In these embodiments, the one or more positioning features can include a safety stop to prevent a positioning device from advancing beyond a planned depth into the bone.

The location of a positioning feature comprised in the guiding instruments according to the present invention is determined based on anatomical features of the bone, the desired position of the guiding instrument on the pelvic bone and the structure of the guiding instrument. The one or more positioning features may be provided either on the support structure or on one of the contact elements of the guiding instrument (or on both). In a particular embodiment, the positioning feature is a slot provided on one of the contact elements. The positioning feature(s) is(are) located on the guiding instrument such that the guiding instrument, when the positioning device is locked into the one or more positioning features, is in the desired position.

The invention further provides methods for manufacturing the guiding instruments described herein.

As detailed above, in particular embodiments, the guiding instruments contain contact elements which are designed such as to ensure a tight fit of the guiding instrument on the bone surrounding the acetabulum. In particular embodiments, this is ensured by designing the guiding instrument or at least the contact elements based on pre-operative images of the bone surrounding the acetabular implant zone and the implant to be introduced therein. Accordingly, methods for producing the (patient-specific) guiding instruments according to the invention typically comprise the step of (a) obtaining volume information of the pelvic bone and the acetabular implant to be placed therein, (b) identifying and selecting parts of the bone surrounding the implant zone which are suitable for use as a base for the contact elements of the guiding instrument, and (c) producing a guiding instrument based on the information obtained in steps (a) and (b). In particular embodiments, step (b) comprises identifying and selecting parts of the bone surrounding the implant zone which contain sufficient features such that the fit of the contact elements with the bone is patient-specific.

Typically, the step of identifying and selecting parts of the bone surrounding the implant zone suitable for use as a base for the contact elements comprises selecting a part of the ilium, ischium and pubic bone of the pelvis suitable for use as a base for a contact element.

The method for manufacturing the guiding instruments according to the invention may further comprise the step of identifying and selecting a suitable position for the placement of a positioning device and the corresponding positioning feature in the guiding instrument.

The step of obtaining volume information of the pelvic bone and the acetabular implant to be placed typically comprises obtaining digital patient-specific image information which can be done by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

In a particular embodiment, Additive Manufacturing (AM) techniques are used for manufacturing the guiding instrument according to the invention. Additive Manufacturing (AM) can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The guiding instruments according to the present invention may be manufactured in different materials. Typically, only materials that are biocompatible (e.g. USP class VI compatible) with the human body are taken into account. Preferably the surgical template is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

According to the present invention guiding instruments are provided for use with an acetabular cup implant, whereby the guiding instrument and the implant are typically interconnected prior to placement of the implant. Accordingly, the present invention also provides combinations of an acetabular cup implant and a guiding instrument according to the present invention. Accordingly, the present invention provides a combination of an acetabular cup implant and a guiding instrument, wherein the guiding instrument comprises (i) a support structure which fits securely onto the acetabular cup implant and (ii) one or more contact elements which are designed to fit onto specific areas of the bone surrounding the acetabular cup implant zone, wherein the contact elements are designed in such a way that they contact the bone in at least three contact points, whereby the angle between the plane through the central axis of the implant and one contact point and the plane through the central axis and the adjacent contact point is never greater than 180° and that, upon contacting the bone surrounding the acetabulum, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum.

The acetabular cup implants for use in the context of the present invention can be standard implants or can be patient-specific, i.e. designed based on specific features of a patient's pelvic zone and/or the damage thereto. In particular embodiments, the acetabular cup implants for use in the context of the present invention are press-fit implants. Acetabular cup implants are known to the skilled person and most types of known press-fit acetabular cup implants are suitable for use in the context of the present invention.

In particular embodiments, the acetabular cup implant is a patient-specific implant which has been designed based on specific features of the patient obtained by medical images of the patient's acetabular implant zone. As described above, methods for obtaining medical images useful for designing an implant are known to the skilled person and include, but are not limited to computer tomography (CT) scanner, a magnetic resonance imaging (MRI) scanner, an ultrasound scanner, or a combination of Roentgenograms. Reference can again by made to the publication by P. Suetens (2002) referred to above.

Irrespective of the locking features described herein below, the outer surface of the acetabular cup implant may comprise a rough texture which mechanically engages the bone and ensures a lock between the implant and the acetabulum. Such a rough texture may be e.g. irregular or comprise a homogenous granular structure or a pattern of ribs and grooves.

The attachment of the guiding instrument to the implant in the combinations of an acetabular cup implant and a guiding instrument according to the present invention may be achieved by any suitable means, such as for instance by one or more locking features or elements. The one or more locking features or elements may for example be present on the guiding instrument, such as on the support structure of the guiding instrument. In these particular embodiments, the guiding instruments according to the invention comprise one or more locking features, which ensure an interlock with the acetabular cup implant. Where the support structure of the guiding instruments of the present invention (designed to fit into an acetabular cup implant) comprises a ring structure designed to fit onto the rim of the implant, such locking features can be positioned on the ring structure to ensure a specific interlock with the acetabular rim of the implant. The one or more locking features may be three-dimensional features designed specifically for every individual guiding instrument/implant combination, or may be standard features such that a modular guiding instrument can fit on a standard implant or on different patient-specific implants.

Additionally or alternatively, the one or more locking features interconnecting the guiding instrument and the implant prior to placement of the implant are provided on the acetabular cup implant. Such locking features are typically positioned on the rim of the acetabular cup implant, but may also be provided in the inner surface (i.e. surface not contacting the pelvic bone) of the hemisphere of the implant to ensure a specific interlock with the guiding instrument according to the invention.

Additionally or alternatively, one or more locking features interconnecting the guiding instrument and the implant prior to placement of the implant may be present on or may be designed to interact with locking features of another element or device. For instance, where the guiding elements are envisaged for use with an impactor such as the impactors of the present invention, one or more locking features may be present on or designed to interact with locking features of the impactor. In this way, the guiding instrument, acetabular cup implant and impactor can be interlocked such that the three form a rigid assembly.

Suitable examples of interacting locking features include, but are not limited to slots and tabs or hooks. Optionally, the locking features comprise a mechanism by which the interlocked parts can be easily released from each other. In particular embodiments, where the locking features ensure a rigid interlock between guiding instrument, implant and impactor prior to placement, a mechanism is optionally provided by which the implant is easily released from the guide and/or the impactor after placement. Non-limiting embodiments of suitable systems for releasing an acetabular cup implant from an impactor are described, for example in US20040153063 and US20070173856.

In a further aspect, the present invention provides surgical impactors for joint implants, which allow a correct, accurate and stable placement and orientation of an implant into the joint. More particularly, the present invention provides impactors which provide an ease of manipulation in a limited operation window, facilitating accurate and stable insertion of a press-fit acetabular cup implant into a patient's acetabulum during hip joint surgery procedures.

The impactors according to the present invention for press-fitting an acetabular cup implant comprise (i) a stem comprising a drive member, a hinge element and an impact element and (ii) a fixation element which locks onto the implant and/or onto a guiding instrument for the implant. The different elements of the stem may be provided as separate interconnected parts but may also correspond to different regions of a device comprising one or more parts.

In the impactors according to the present invention, the hinge element of the stem forms a ball joint with the fixation element allowing movement of the orientation of the stem relative to the fixation element. Indeed, the impactors of the present invention are designed in such a way that the stem can freely rotate with respect to the fixation element around the center point of the implant. This enables the surgeon to orient the stem of the impactor in different directions with respect to the acetabular cup implant and/or a guiding instrument for the acetabular cup implant.

The different components of the impactors according to the present invention are described more in detail hereafter.

As described above, the impactors according to the present invention comprise a stem and a fixation element. The stem of the impactors according to the invention comprises a drive member, a hinge element and an impact element. The impact element of the stem receives the impacts that are given by means of an impacting device.

The drive member typically has a longitudinal shape (such as a shaft), allowing the surgeon to have a good grip on the impactor for positioning in the direction/orientation in which the impacts will be given. According to specific embodiments, the drive member of the stem is a roughly cylinder-shaped longitudinal element.

The stem of the impactors according to the invention further comprises a hinge element, which is a ball-shaped element attached to the end of the drive member. The hinge element of the stem of the impactors of the present invention is locked into the fixation element (described below) of the impactor by forming a ball joint. This ball joint serves to transfer the impacts (given to the drive member of the stem) evenly to the fixation element of the impactor and hence to the acetabular cup implant and/or guiding instrument connected thereto (as described in detail below).

The impactors according to the present invention also comprise a fixation element. This fixation element is designed a) to ensure a ball-joint with the hinge element of the impactor and b) to fit onto an acetabular cup implant and/or guiding instrument for an acetabular cup implant. Accordingly, the impactors according to the invention further typically contain not only a general shape which is complementary to the shape of an acetabular cup implant and/or guiding element of an acetabular cup implant but in addition one or more locking features which allow a tight interlock with a guiding instrument for an acetabular implant and/or with an acetabular cup implant.

The part of the fixation element forming the ball joint with the hinge element of the stem generally has an essentially spherical shape, adjusted to closely mate with the ball shape of the hinge element, whereby at least one opening is provided to allow passage and movement of the drive member. In particular embodiments, the opening allows for movement of the drive member in any direction. In alternative embodiments, the opening in the fixation element limits the movement of the stem to particular orientations. In a particular embodiment, the opening is provided such that the stem and/or the fixation element can rotate freely (with respect to each other) around the center point of the implant.

In particular embodiments of the impactors of the present invention, the stem and/or fixation element further comprise a locking element that can limit or fully block the movement of the stem relative to the fixation element. Such a locking element allows the surgeon to easily fix a pre-determined desired orientation and/or position of the stem of the impactor relative to the fixation element (and accordingly relative to the implant and/or the guiding instrument for the implant attached or interconnected thereto). Suitable examples of locking elements include but are not limited to a clasp extending from the fixation element or a slot in the fixation element which can be used to fix the position of the stem. In a particular embodiment a locking element is provided onto the drive member of the impactor, wherein said locking element can be moved along the drive member until it makes contact with the fixation element, thereby locking the position of the stem within the fixation element. When locked, the position of the stem with regard to the fixation element may be provided at any angle ranging from 0° (the stem being locked into the fixation element in the upright position) to 90° (the orientation of the stem forming a right angle with the x-axis of the fixation element). In further particular embodiments the drive member of the stem is threaded, and the locking element is fitted onto this thread and can thus be rotated towards the opening of the fixation element to block the movement of the stem.

As detailed above, the impactors according to the present invention, and more particularly the fixation elements thereof are designed to fit securely either directly onto an acetabular cup implant or onto a guiding instrument for an acetabular cup implant (optionally in combination with the acetabular cup implant). Where the impactor is designed to fit directly onto an acetabular cup implant the outer shape of the ball-joint structure of the fixation element is typically also hemispherical in shape, to match the shape of the implant. Where the impactor is designed to fit onto a guiding instrument for an acetabular cup implant, the outer shape of the ball-joint structure of the fixation element is determined by the shape of the guiding instrument. Typically, where the shape of the guiding instrument follows that of the implant (corresponding to a hollow hemisphere), the shape of the fixation element is also hemispherical. The corresponding concentrical shapes of the fixation element and guide allow an even transfer of an impact given to the stem of the impactor to the whole of the implant.

The impactors according to the invention typically further comprise one or more locking features which by themselves allow locking of the impactor to an acetabular cup implant and/or a guiding instrument for an acetabular cup implant, or can interact with locking features present on an acetabular cup implant and/or a guiding instrument for an acetabular cup implant to ensure a rigid assembly. The one or more locking features may be three-dimensional features designed specifically for an impactor/implant and/or guiding instrument combination. Additionally or alternatively, the locking features may allow the interlock of a standard impactor with a patient-specific guide and/or patient-specific implant, with a customized guide and/or a patient-specific implant, or with standard guides and implants.

The impactors according to the present invention may further comprise a mechanism to easily release the implant and/or the guiding instrument for the implant after the implant has been correctly placed into the patient's acetabulum (as described above).

The impactors according to the invention can be produced in different materials using methods known to the skilled person. Typically, at least the stems and the fixation elements of the impactors are produced in rigid material, such as metal, to withstand the force from blows of a hammer or the like.

The present invention further provides combinations of an acetabular cup implant and an impactor as described herein, wherein the impactor comprises (i) a stem comprising a drive member, a hinge element and an impact element and (ii) a fixation element which locks onto the implant and/or onto a guiding instrument for the implant, wherein the hinge element of the stem forms a ball joint with the fixation element allowing movement of the orientation of the stem relative to the fixation element and wherein said fixation element of said impactor locks onto said implant. Indeed, according to particular embodiments, impactors are provided which are designed to fit directly onto an acetabular cup implant. The implant is locked onto the impactor prior to placement of the implant and released therefrom after the implant has been positioned.

In these embodiments, the impactor and/or the acetabular cup implant contain one or more features which either alone or together allow a tight interlock of the impactor and implant forming a rigid assembly. In particular embodiments, the fixation element of the impactor contains one or more locking features, such as hooks, which fit into corresponding slots present on the implant. Optionally, a mechanism is provided by which the implant can be easily released from the impactor after placement.

The present invention further provides a combined guiding and fitting element for an acetabular cup implant. More particularly, the combined guiding and fitting element for an acetabular cup implant comprises a guiding instrument and an impactor. In particular embodiments, the combined guiding and fitting element comprises a guiding instrument according to the invention, i.e. a guiding instrument for an acetabular cup implant comprising (i) a support structure which fits securely onto the acetabular cup implant and (ii) one or more contact elements which fit onto areas of the bone surrounding the acetabular cup implant zone in at least three contact points. The contact elements are designed in such a way that the angle between the plane through the central axis of the implant and one contact point and the plane through the central axis and the adjacent contact point is never greater than 180°. Moreover the one or more contact elements are designed such that, upon contacting, the one or more contact elements and the specific areas of the bone surrounding the acetabulum engage by means of a unique and tight fit, which is ensured by the complementarity between at least one of the one or more contact elements and the patient-specific morphology of the specific areas of the bone surrounding the acetabulum. The combined guiding and fitting element further comprises an impactor. In further particular embodiments, the combined guiding and fitting element according to the invention comprises an impactor as described herein, i.e. an impactor which comprises (i) a stem comprising a drive member, a hinge element and an impact element and (ii) a fixation element which locks onto the implant and/or onto a guiding instrument for the implant, wherein the hinge element of the stem forms a ball joint with the fixation element allowing movement of the orientation of the stem relative to the fixation element and wherein the fixation element of the impactor interconnects with said guiding instrument. The combined guiding and fitting element further comprises a guiding instrument. In most particular embodiments, the combined guiding and fitting element according to the invention comprise both a guiding instrument for an acetabular cup implant and an impactor as described herein, wherein the guiding instrument and impactor can interlock to form a rigid assembly. This is ensured by (a) the fact that outer shape of the fixation element is adjusted to fit on the shape of the guiding instrument, more particularly on the support structure of the guiding instrument and by (b) one or more locking features present on the impactor and/or the guiding instrument which can ensure a tight interlock of these two elements. In particular embodiments, the fixation element of the impactor contains one or more hooks which fit into corresponding slots present on the guiding instrument. Optionally, a mechanism is provided by which the guiding instrument can be easily released from the impactor.

The present invention further provides combinations of an acetabular cup implant and a combined guiding and fitting element for an acetabular cup implant. In the most particular embodiments of this combination, the guiding and fitting element comprises (a) a guiding instrument for the acetabular cup implant and an impactor which can form a rigid assembly with the implant prior to placement thereof. More particularly, the guiding instrument is a guiding instrument as described herein comprising (i) a support structure which fits securely onto an acetabular cup implant and (ii) one or more contact elements which fit onto areas of the bone surrounding the acetabular cup implant zone in at least three contact points, wherein the contact elements are designed in such a way that the angle between the plane through the central axis of the implant and one contact point and the plane through the central axis and the adjacent contact point is never greater than 180°. More particularly, the guiding element comprises three or more contact elements which are designed in such a way that the angle between the plane through the central axis of the implant and one contact element and the plane through the central axis and the adjacent contact element is never greater than 180°. Moreover, the contact elements are designed such that upon contacting the specific areas of the bone surrounding the acetabulum, engage with the specific areas of the bone surrounding the acetabulum by means of a unique and tight fit, which is ensured by the complementarity between at least one of the one or more contact elements and the patient-specific morphology of the specific areas of the bone surrounding the acetabulum. The impactor envisaged in this combination is an impactor which comprises (i) a stem comprising a drive member, a hinge element and an impact element and (ii) a fixation element which locks onto the implant and/or onto a guiding instrument for the implant, wherein the hinge element of the stem forms a ball joint with the fixation element allowing movement of the orientation of the stem relative to the fixation element and wherein the fixation element of the impactor interconnects with the guiding instrument. The acetabular cup implant for use in the combinations according to the invention is an acetabular cup implant such as is known to the skilled person. In particular embodiments the acetabular cup implant contains one or more locking features which can ensure that the guiding instrument, impactor and implant form a rigid assembly.

A further aspect of the present invention provides methods of ensuring accurate placement of an acetabular implant cup, which involve the use of the guiding instruments, impactors and combinations thereof according to the invention. In particular embodiments, a combination of an acetabular implant cup, a guiding instrument for the acetabular implant cup and an impactor is used, which is designed such that the elements can interlock and form a rigid structure. Before the placement of an implant, the implant and guiding instrument are attached to the fixation element of the impactor. The implant is guided toward the acetabular implant zone manually by the surgeon. The fixation element of the impactor (which is interlocked with the guiding instrument and the implant) can rotate freely with respect to the stem, making it possible to position the guide and implant in the desired orientation, irrespective of the available surgical window.

Optionally, the guiding element is positioned with the help of a positioning instrument which interlocks or matches with a positioning feature on the guide. More particularly, a guiding pin is introduced into a corresponding slot on the guiding instrument, which helps to position the implant and guide. Additionally or alternatively, in particular embodiments, the guiding instrument, and more particularly the contact surfaces thereof are designed in such a way that, upon insertion of the implant, the implant is forced to rotate around its center point into the desired orientation in order for the contact elements to fit onto the corresponding structures of the surrounding bone.

The impactor, more particularly the stem of the impactor, is hit with a hammer in order to fit the implant into the (reamed) acetabular implant zone. Optionally, the movement of the stem of the impactor is blocked by a locking element, prior to administering the impacts to the impactor.

After insertion of the implant in the desired position, both impactor and guiding instrument are released from the implant.

The present invention further provides methods of ensuring accurate placement of an acetabular implant cup which involve the use of the guides and/or impactors according to the invention, which are designed to interlock into a rigid assembly with the implant.

Typically, the guiding instruments of the present invention have been manufactured based on a three-dimensional image of the acetabular implant zone of the pelvis of a patient such that they accurately fit onto the pelvis bone in the desired position in a unique way. In particular embodiments, the contact elements are designed such that upon placement of the guiding instrument in the acetabular implant zone, the guiding instrument and the acetabular cup implant are either forced to or can be made to rotate around the implant's center point until the implant has the desired orientation with respect to the pelvis. Accordingly, particular embodiments of the methods for ensuring accurate placement of the acetabular implant cup according to the invention comprise bringing the guiding instruments with the implant connected thereto in the acetabular implant zone of the patient and pressing the guiding instrument with a rotating movement such as to bring the guiding instrument and implant in the position wherein the contact elements fit uniquely with the corresponding bone structure.

In particular embodiments, the guiding instruments according to the invention comprise a positioning feature. In further particular embodiments, the guiding instrument is used for the placement of a positioning device. In these embodiments, the guiding instrument is provided with a positioning feature, which corresponds to a location which based on the bone structure and the operation window is appropriate for placement of the positioning device. Accordingly, in these embodiments, the guiding instrument is brought onto its unique position in the pelvic bone of the patient. Thereafter, a positioning device, such as a positioning pin, is introduced into the positioning feature of the guide and introduced into the bone. Optionally, the guiding instrument is then removed from the pelvic bone, leaving the positioning device in place. This positioning device is of use to the surgeon for the orientation of the impactor when applying force thereto.

In alternative embodiments, the positioning device is placed into the pelvic bone prior to placement of the guiding instrument and can be used to place the guiding instrument in the desired position.

Upon use of the impactors according to the invention, the rotation of the stem of the impactor relative to the fixation element (and the implant connected thereto) facilitates accurate placement of the implant irrespective of the available surgical window. More particularly, in certain embodiments, in order to facilitate the placement of the acetabular cup implant through the limited surgical window, the orientation of the stem is moved such that it no longer corresponds to the x-axis of the implant. Optionally, a locking element present on the impactor then allows locking of the stem, to ensure that upon application of force, the implant is fitted into the correct position.

The impactor, more particularly the impact element of the stem is hit with a hammer in order to fit the implant into the (reamed) acetabular implant zone. After insertion of the implant in the desired position, the impactor is released from the implant (and where applicable, from the guiding instrument), typically by way of a mechanism which provides a control over the locking features present on the impactor and/or implant (and guiding instrument).

The different aspects of the invention are illustrated herein by the following non-limiting embodiments.

According to particular embodiments, a guiding instrument (1) is provided, such as illustrated in FIG. 1, comprising a supporting structure (2) which fits securely onto an acetabular cup implant and three contact elements (3), each of which comprise a contact point which fits onto an area of the bone surrounding the acetabular cup implant zone. The contact elements are designed such that the angle between the plane through the central axis of the implant (X, see FIG. 3) and one contact point and the plane through the central axis (X) and the adjacent contact point is never greater than 180°. In addition, the contact elements (3) ensure a tight fit of the guiding instrument on said bone.

In particular embodiments, the guiding instrument contains one or more guide holes (4), i.e. openings which serve as a locking feature engaging with a locking feature of the impactor and ensure a direct transfer of the impact to the implant.

In particular embodiments, the guiding instrument contains one or more positioning features (5), e.g. holes or slots allowing the passage of a positioning device in the bone surrounding the acetabulum. In particular embodiments, the positioning feature (5) is a slot present in one of the contact elements (3) of the guiding instrument (1).

In particular embodiments, the guiding instrument contains one or more locking features (6) which allow an interlock of the guiding instrument with an implant and/or an impactor as further described herein. In particular embodiments, the locking features are positioned on a ring structure (7) of the supporting structure which fits onto the rim of the acetabular implant.

Figure 2:
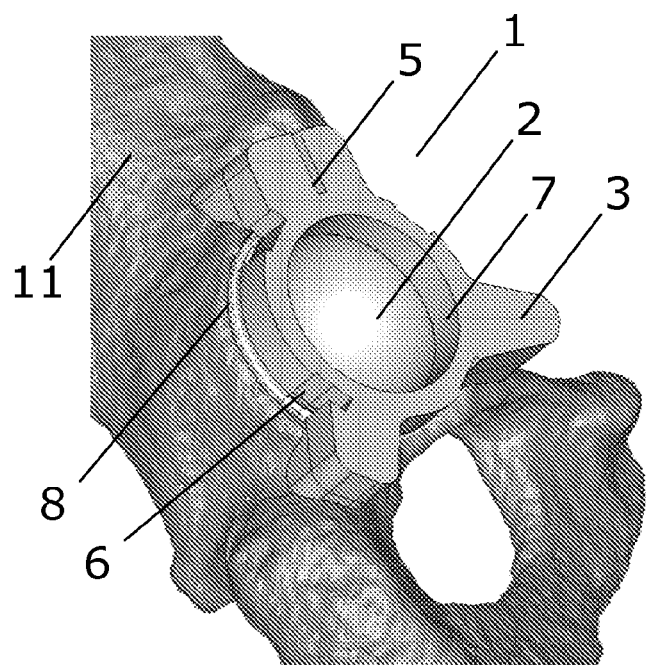
FIG. 2 The guiding instrument (1) and implant (8) according to a particular embodiment of the invention shown after insertion into the pelvis. On the guiding instrument (1), the support structure (2) comprising a ring structure (7) interconnecting the contact elements (3). One of the contact elements comprises a positioning feature (5) and the ring structure of the support structure comprises locking features (6).

In further particular embodiments, the invention provides combinations of acetabular cup implants (8) and guides for acetabular cup implants (1). A pelvic bone (11), in which an assembly of an acetabular cup implant (8) and guide instrument (1) is positioned is illustrated in FIG. 2.

Figure 3:
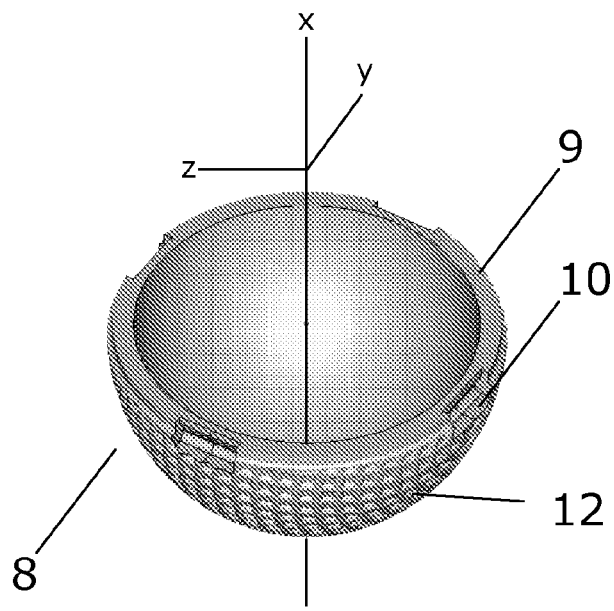
FIG. 3 The implant (8) according to particular embodiments of the invention comprising a rim (9) with locking features (10). The central axis of the implant is indicated as X.
Figure 4:
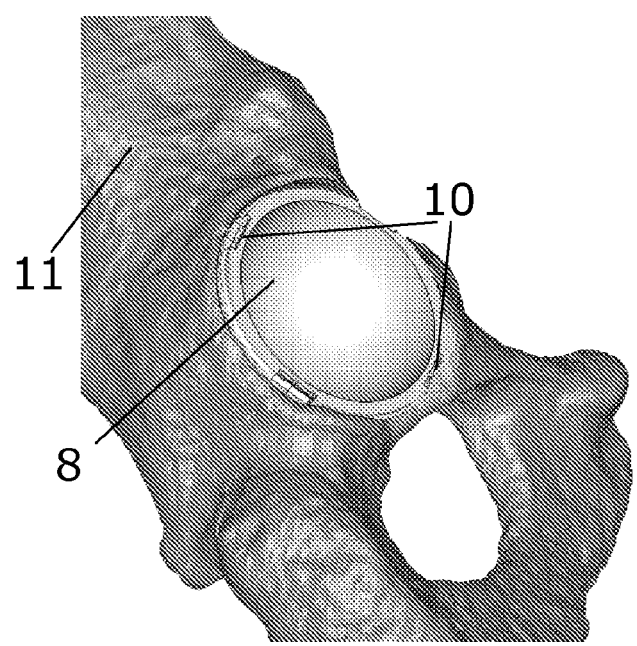
FIG. 4 View of an implant (8) inserted into the pelvic bone (11) according to a particular embodiment of the invention. The locking features (10) present on the rim of the implant are visible.

The acetabular cup implants for use in these embodiments may be standard or patient-specific. An acetabular cup implant is schematically represented in FIG. 3. Typically such an implant contains a surface texture on the outer surface (12) to ensure an interlock with the bone. Optionally, the acetabular cup implant contains one or more locking features (10) which allow the interlock thereof with a guiding instrument and/or an impactor according to the invention. Typically, these locking features (10) are positioned in the rim (9) of the acetabular implant cup. The acetabular cup implants fit securely into the pelvic bone in the reamed acetabulum (as illustrated in FIG. 4).

Figure 5:
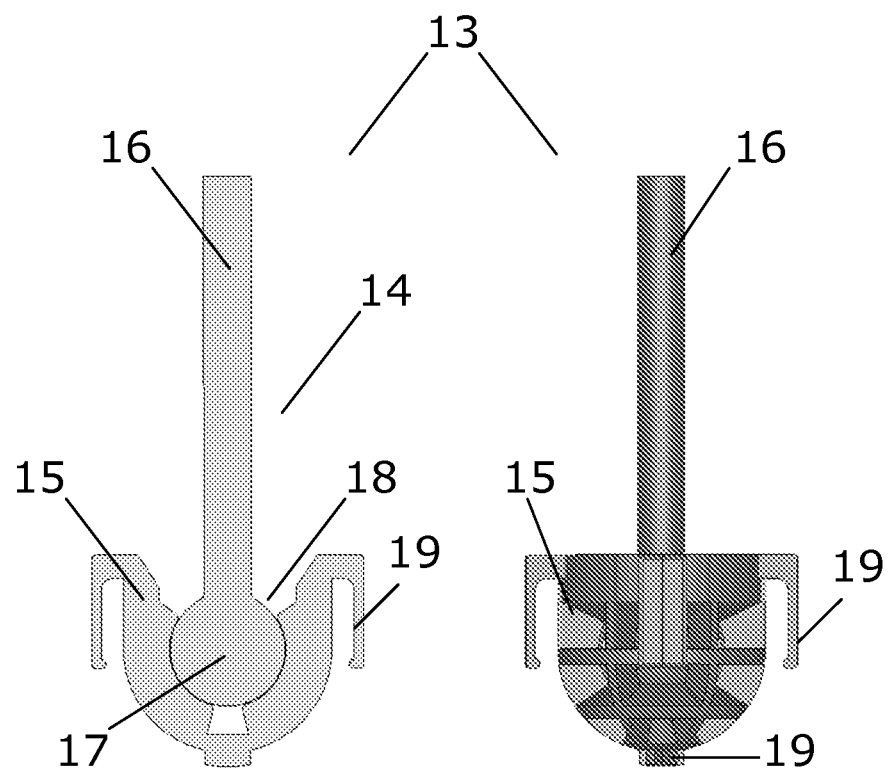
FIG. 5 Section view (left) and side view (right) of an impactor (13) according to particular embodiments of the invention comprising a stem (14) and a fixation element (15). The stem comprises a drive member (16), an impact element (17) and a hinge element (20) which forms a ball joint with the fixation element (15). The opening (18) of the fixation element allows passage of the stem and movement thereof relative to the fixation element. The fixation element further comprises locking features (19) for locking onto a guiding instrument and/or acetabular cup implant.
Figure 10:
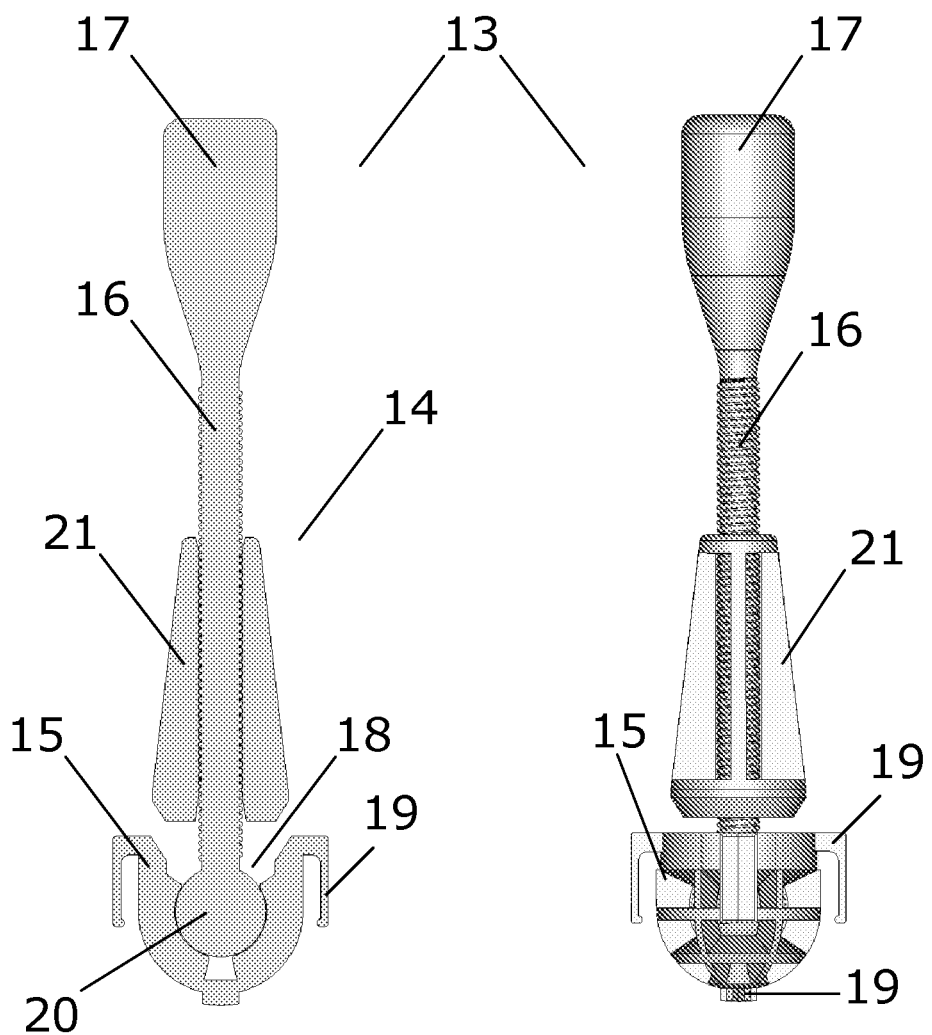
FIG. 10 Section view (left) and side view (right) of an impactor (13) according to particular embodiments of the invention comprising a stem (14) and a fixation element (15). The stem comprises a drive member (16), an impact element (17) and a hinge element (20) which forms a ball joint with the fixation element (15). The opening (18) of the fixation element allows passage of the stem and movement thereof relative to the fixation element. The impactor further comprises locking element (21) for locking the stem in a particular position in the fixation element.

The invention further provides impactors (13), such as illustrated in FIG. 5 comprising a stem (14) and a fixation element (15). The stem (14) comprises a drive member (16), a hinge element (20) and an impact element (17). The hinge element (20) of the stem forms a ball joint with the fixation element (15) allowing movement of the orientation of said stem relative to the fixation element. The fixation element (15) contains an opening (18) which allows the passage and movement of the stem of the stem of the impactor. In particular embodiments, such as illustrated in FIG. 10, the invention provides impactors (13) comprising a locking element (21) positioned on the drive member (16) of the stem (14) which can be used to block the movement of the stem relative to the fixation element.

The fixation element (15) further contains an outer shape which corresponds to the shape of a guide instrument and/or an acetabular cup implant.

The fixation element may comprise one or more locking features (19) which engage with a guide for an acetabular cup implant and/or an acetabular cup implant.

Figure 6:
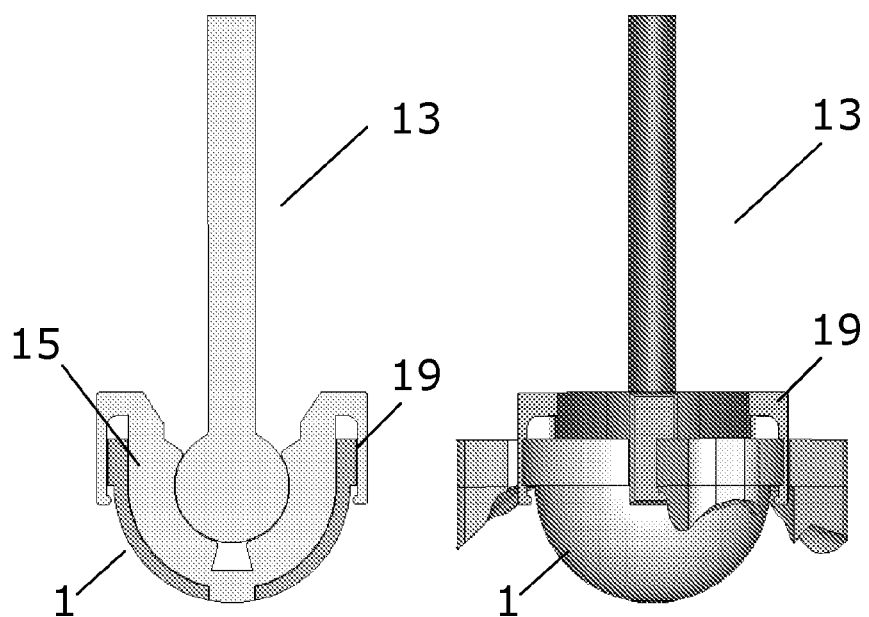
FIG. 6 Section view (left) and side view (right) of a guiding instrument (1) and impactor (13) assembly, whereby the fixation element (15) of the impactor comprises locking features (19) which interlock with the guiding instrument (1).
Figure 11:
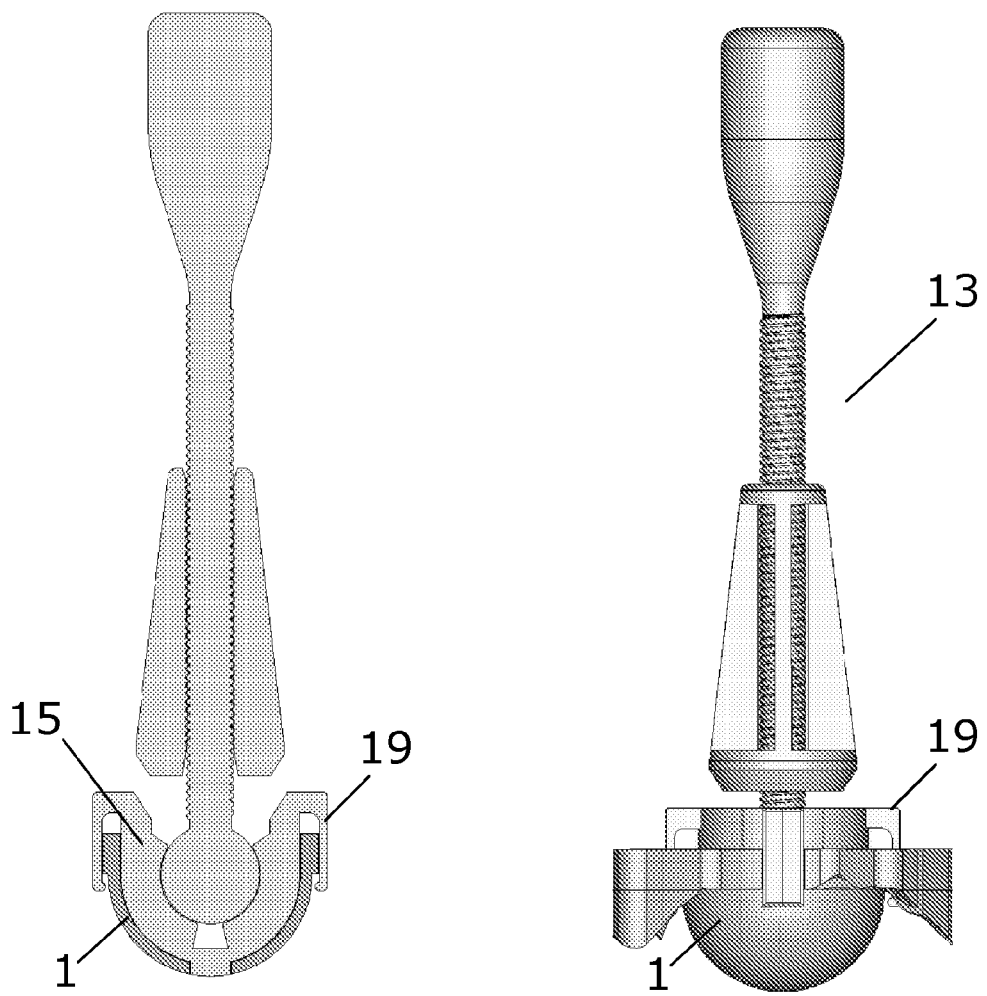
FIG. 11 Section view (left) and side view (right) of a combined guiding and fitting instrument according to particular embodiments of the invention wherein the combined guiding and fitting instrument comprises a guiding instrument (1) and an impactor (13) assembly. Locking features (19) on the fixation element (15) of the impactor lock onto the guiding instrument (1) ensuring a rigid assembly of the impactor (13) and the guiding instrument (1).

The invention further provides combinations of a guide for an acetabular cup implant (1) and an impactor (13) according to the invention. An assembly of an acetabular cup implant interlocked with an impactor is illustrated in FIG. 6. There is a close fit between the cup of the implant guide (1) and the fixation element (15) of the impactor. A secure interlock is further ensured by locking features (19) on the fixation element (15) which optionally interlock with corresponding features on the guiding instrument. In a particular embodiments, such as illustrated in FIG. 11 the invention provides combinations of a guide for an acetabular cup implant (1) and an impactor (13) wherein the impactors (13) comprise a locking element (21) positioned on the drive member (16) of the stem (14) which can be used to block the movement of the stem relative to the fixation element.

Figure 7:
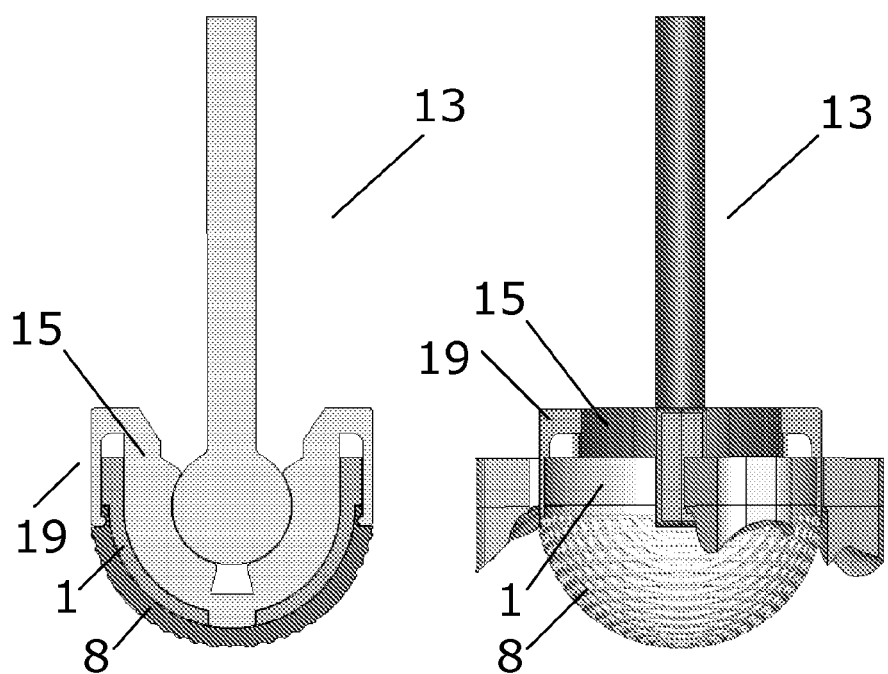
FIG. 7 Section view (left) and side view (right) of a combined guiding and fitting instrument and acetabular cup implant (8) according to particular embodiments of the invention wherein the combined guiding and fitting instrument comprises a guiding instrument (1) and an impactor (13). The outer surface of the fixation element (15) of the impactor corresponds to the shape of the support structure of the guiding instrument (1), which itself corresponds to the inner shape of the implant (8). Locking features (19) on the fixation element (15) of the impactor lock onto the guiding instrument (1) and the implant (8) ensuring a rigid assembly of impactor, guiding instrument and implant.
Figure 8:
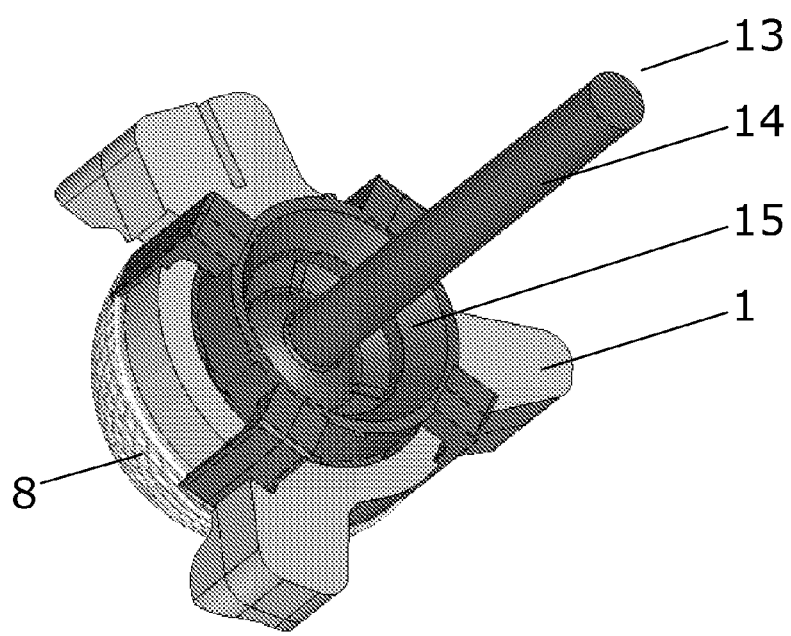
FIG. 8 Combined guiding instrument (1) and implant (8) connected to the fixation element of an impactor (13) according to a particular embodiment of the invention. The guiding instrument (1) comprises a stem (14) and a fixation element (15) which are interconnected by a ball joint.

In particular embodiments of the invention, impactors (13) are provided which can form a rigid assembly with a guide for an acetabular cup implant (1) and a corresponding acetabular cup implant (8), such as illustrated in FIGS. 7 and 8. The outer shape of the fixation element (15) and the cup of the guide (1) are hemispherical to correspond with the shape of the implant (8).

Figure 9:
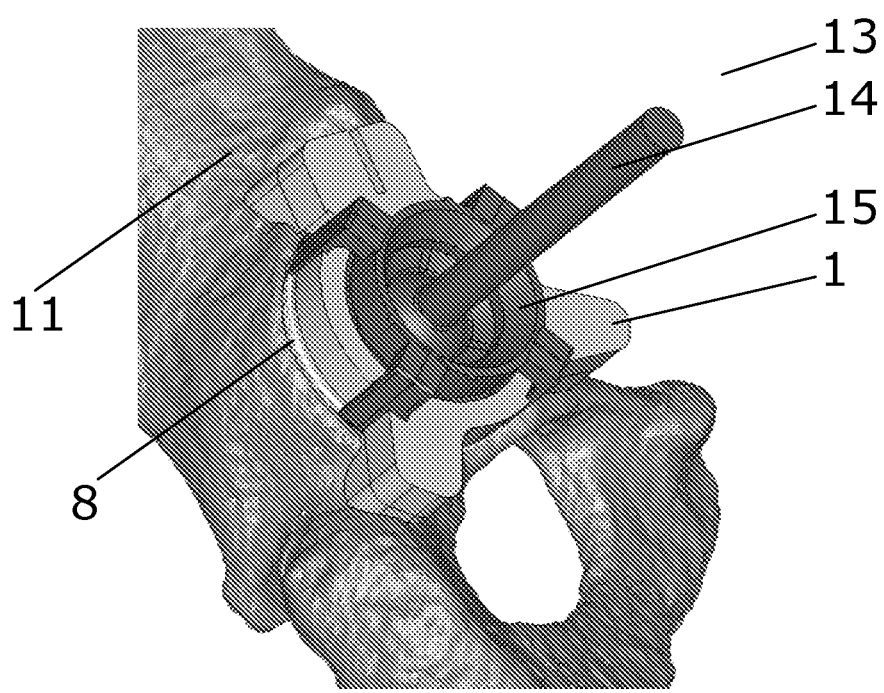
FIG. 9 View of a combined guiding and fitting instrument and acetabular cup implant (8) inserted into the pelvic bone (11) according to a particular embodiment of the invention. The combined guiding and fitting instrument comprises a guiding instrument (1) and an impactor assembly (13), the latter comprising a stem (14) and a fixation element (15).

FIG. 9 illustrates an assembly of an implant (8), implant guiding instrument (1) and impactor (13) (comprising a stem (14) and fixation element (15)) according to the invention, positioned in a pelvic bone (11).

Figure 12:
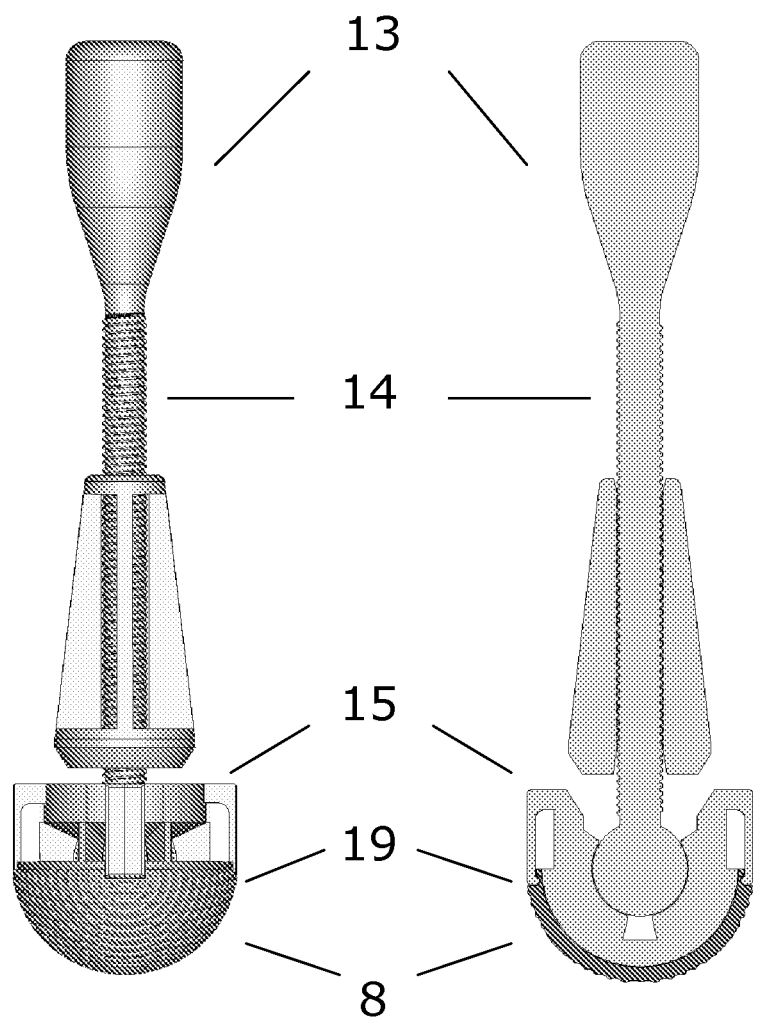
FIG. 12 Section view (left) and side view (right) of a combined impactor (13) and implant (8) according to particular embodiments of the invention. The impactor comprises a stem (14) and a fixation element (15). Locking features (19) on the fixation element (15) of the impactor lock onto the implant (8) ensuring a rigid assembly of the impactor (13) and the implant (8).

The invention further provides combinations of an implant (8) and an impactor (13) designed to fit on the implant, such as illustrated in FIG. 12. The impactors comprise a stem (14) and a fixation element (15). The fixation element (15) contains locking features (19) which interlock with corresponding features on the implant.

The invention claimed is:

1. A combined guiding and fitting element configured for an acetabular cup implant (8), said combined guiding and fitting element comprising :
  i) a guiding instrument (1) which comprises:
    a hollow support structure (2) having an inner surface that is designed to fit with the outer surface of a fixation element (15) of an impactor (13) and an outer surface configured to fit securely onto the acetabular cup implant (8), and
    one or more contact elements (3) configured to fit onto areas of the bone surrounding the acetabular cup implant zone in at least three contact points,
  wherein
    the one or more contact elements (3) are designed such that the angle between the plane through the central axis of the implant (8) and one contact point and the plane through the central axis and the adjacent contact point is never greater than 180°; —and said one or more contact elements (3) configured to engage said specific areas of the bone surrounding the acetabulum by means of a unique and tight fit; ensured by a complementarity between at least one of said one or more contact elements (3) and the patient-specific morphology of the bone surrounding the acetabulum, and ii) an impactor (13) configured to press-fit an acetabular cup implant (8) comprising:
a stem (14) comprising a drive member (16), a hinge element (20) and an impact element (17); and
a fixation element (15),
wherein said hinge element (20) of the stem (14) forms a ball joint with said fixation element (15) allowing movement of the orientation of said stem (14) relative to said fixation element (15);
wherein said combined guiding and fitting element comprises one or more locking features (6), (19), for interlocking of said guiding instrument (1) and said impactor (13).

2. The combined guiding and fitting element according to claim 1, wherein said one or more locking features include one or more hooks (19) present on said fixation element (15), for fixing said impactor onto said guiding element.

3. The combined guiding and fitting element according to claim 1, wherein said contact elements (3) of said guiding instrument (1) are designed such that, upon placement of said combined guiding and fitting element onto the bone, said element is forced to rotate around its center point until said one or more contact elements (3) and said specific areas of the bone surrounding the acetabulum engage by means of a unique and tight fit such that the implant has the wanted orientation with respect to the pelvis.

4. The combined guiding and fitting element according to claim 1, wherein said guiding instrument (1) further contains a positioning feature (5) allowing the passage of a positioning device placed in the bone surrounding the acetabulum.

5. The combined guiding and fitting element according to claim 4, wherein said positioning device is a pin placed in the bone surrounding the acetabulum.

6. The combined guiding and fitting element according to claim 1, wherein two or more of said contact elements (3) form larger contact surfaces extending over specific areas of the bone surrounding the acetabulum.

7. The combined guiding and fitting element according to claim 1, wherein the guiding instrument (1) is a medical-image-based patient-specific instrument.

8. The combined guiding and fitting element according to claim 1, wherein the guiding instrument (1) is a modular device comprising elements with a standard shape that can be adjusted to the shape of the bone.

9. The combined guiding and fitting element according to claim 1, wherein said impactor (13) further comprises a locking element (21) that can limit or fully block the movement of the stem (14) relative to the fixation element (15).

10. The combined guiding and fitting element according to claim 1, wherein said impactor (13) further comprises a mechanism to easily release the guiding instrument (1) from the implant (8).

11. A combination of an acetabular cup implant (8) and a combined guiding and fitting element according to claim 1.

12. The combination of an acetabular cup implant (8) and a combined guiding and fitting element according to claim 11, wherein said combined guiding and fitting element and said implant (8) comprises one or more locking features for interlocking with said combined guiding and fitting element.

13. The combination of an acetabular cup implant (8) and a combined guiding and fitting element according to claim 12, wherein said one or more locking features include one or more hooks (19) present on said fixation element (15), for fixing said impactor onto said guiding instrument (1) and said implant (8).

14. A guiding instrument (1) configured for an acetabular cup implant (8), said guiding instrument comprising:
a hollow support structure (2) having an inner surface that is designed to fit with the outer surface of a fixation element (15) of an impactor (13) and an outer surface configured to fit securely onto an acetabular cup implant (8), and
one or more contact elements (3) configured to fit onto the patient-specific morphology of areas of the bone surrounding the acetabular cup implant zone in at least three contact points,
wherein said one or more contact elements (3) are designed such that the angle between the plane through the central axis of the implant (8) and one contact point and the plane through the central axis and the adjacent contact point is never greater than 180°;
wherein said one or more contact elements (3) is configured to engage said specific areas of the bone surrounding the acetabulum by means of a unique and tight fit; ensured by the complementarity between at least one of said one or more contact elements (3) configured to engage the patient-specific morphology of said specific areas of the bone surrounding the acetabulum, and
wherein said guiding instrument (1) comprises one or more locking features (6) for fixing of said guiding instrument onto an impactor (13) and/or implant (8), and wherein said guiding instrument (1) further comprises one or more locking features (6), (10) for interlocking with an acetabular cup implant (8).

15. A method for ensuring accurate placement of an acetabular implant cup into the acetabular cup implant zone of a patient, which method comprises:
a) attaching said acetabular implant to an impactor comprising:
a stem (14) comprising a drive member (16), a hinge element (20) and an impact element (17); and
a fixation element (15),
wherein said hinge element (20) of the stem (14) forms a ball joint with said fixation element (15) allowing movement of the orientation of said stem (14) relative to said fixation element (15);
whereby said implant is attached to said impact element of said impactor
b) placing said impactor in a guiding instrument comprising one or more contact elements (3) which fit onto areas of the bone surrounding said acetabular cup implant zone in at least three contact points; and
c) positioning said guiding element on said patient, by placing said contact elements on said areas of the bone surrounding said acetabular cup implant zone.

* * * * *